(12) United States Patent
Sanders

(10) Patent No.: US 7,336,859 B2
(45) Date of Patent: Feb. 26, 2008

(54) SENSOR USING ULTRA THIN WAVEGUIDES AND OPTICAL FIBERS

(75) Inventor: Glen A. Sanders, Scottsdale, AZ (US)

(73) Assignee: Honeywell International, Inc., Morristown, NJ (US)

( * ) Notice: Subject to any disclaimer, the term of this patent is extended or adjusted under 35 U.S.C. 154(b) by 44 days.

(21) Appl. No.: 11/321,158

(22) Filed: Dec. 28, 2005

(65) Prior Publication Data

US 2007/0147732 A1 Jun. 28, 2007

(51) Int. Cl.
*G02B 6/00* (2006.01)
*G02B 6/02* (2006.01)

(52) U.S. Cl. .............................. 385/12; 385/30; 385/32
(58) Field of Classification Search ................ 385/12, 385/30, 32
See application file for complete search history.

(56) References Cited

U.S. PATENT DOCUMENTS

| | | | |
|---|---|---|---|
| 5,633,724 A * | 5/1997 | King et al. ................. | 356/445 |
| 5,663,790 A * | 9/1997 | Ekstrom et al. ............ | 356/128 |
| 6,539,155 B1 | 3/2003 | Broeng et al. | |
| 6,694,067 B1 | 2/2004 | O'Keefe et al. | |
| 6,721,053 B1 * | 4/2004 | Maseeh ...................... | 356/436 |
| 6,909,824 B1 * | 6/2005 | Messica et al. ............. | 385/30 |
| 7,054,009 B2 * | 5/2006 | DePue et al. ............... | 356/437 |
| 7,057,250 B2 * | 6/2006 | Kolodzey et al. ........... | 257/428 |
| 2002/0114578 A1 | 8/2002 | Lin et al. | |
| 2004/0227089 A1 * | 11/2004 | Kolodzey et al. .......... | 250/341.8 |
| 2004/0263856 A1 | 12/2004 | Willig et al. | |
| 2005/0077513 A1 | 4/2005 | Fan et al. | |
| 2005/0094150 A1 * | 5/2005 | DePue et al. ............... | 356/445 |
| 2006/0072875 A1 * | 4/2006 | Bhagavatula et al. ........ | 385/30 |
| 2006/0180762 A1 * | 8/2006 | Kolodzey et al. .......... | 250/341.1 |

FOREIGN PATENT DOCUMENTS

| | | |
|---|---|---|
| EP | 0 240 949 A2 | 10/1987 |
| EP | 1 391 693 A1 | 2/2004 |
| GB | 2222881 A | 3/1990 |

OTHER PUBLICATIONS

PCT International Search Report PCT/US2006/002839, Jun. 6, 2006.
Carroll et al., "The Passive Resonator Fiber Optic Gyro and Comparison to the Interferometer Fiber Gyro" from SPIE Milestone Series, pp. 486-494, (1989).
European Search Report No. 06126297.8 dated May 10, 2007.

\* cited by examiner

*Primary Examiner*—K. Cyrus Kianni
(74) *Attorney, Agent, or Firm*—Ingrassia Fisher & Lorenz

(57) ABSTRACT

Methods and apparatus are provided for detecting one or more contaminant particles in an environment with an optical sensor. The sensor includes at least one optical waveguide in a resonant arrangement and a light source positioned in an environment in which the presence of a contaminant particle is sought to be determined. The at least one optical waveguide is of a diameter that an evanescent tail of the lightwave extending there through extends into the environment and is reactive to at least one contaminant particle in the surrounding environment. A detector is positioned to receive light indicative of the sharpness of the optical resonance lineshape of the optical resonator at a pre-selected optical wavelength. The detected information determines the specific contaminant particle in the environment and the concentration of the contaminant particle in the environment.

9 Claims, 5 Drawing Sheets

SENSOR USING ULTRA THIN WAVEGUIDES AND OPTICAL FIBERS

FIELD OF THE INVENTION

The present invention generally relates to sensors, and more particularly relates to chemical and biological sensors using ultra thin waveguides and optical fibers.

BACKGROUND OF THE INVENTION

In recent years, growing sophistication of terrorist threats to homeland and abroad makes awareness-of chemical and biological substances, including chemical and environmental toxins and biohazardous materials, of great importance. This awareness brings about a need for the accurate sensing and monitoring of these types of substances, especially those that may be present as air-borne particles/molecules and are dangerous to humans. The desired level of sensing sensitivity is that which provides for the accurate sensing of various chemical and biological substances at levels that are considered potentially dangerous, while preventing false alarms for levels of materials that are not considered potentially dangerous.

Biohazardous materials are defined as those substances that are naturally occurring in nature such as SARS, influenza, smallpox, anthrax, plague or the like. Sensing and monitoring the presence of these types of materials provides awareness in both naturally occurring situations and when intentionally used in a hazardous manner. The intentional use of biohazardous materials is referred to as the use of biological agents, such as one or more organisms, or one or more toxins derived from living organisms, against people, animals, or crops. In addition, sensing and monitoring of various chemical and environmental toxins, including pesticides and herbicides, is needed. While these man-made chemical and environmental toxins may provide beneficial qualities when used properly, these toxins may become chemical agents if wrongly used.

Many types of sensors have been developed to detect a variety of chemical and environmental toxins and biohazardous materials, but there are currently more toxic substances and hazardous biological materials that need to be sensed than there are suitably sensitive and discriminating sensors. The most common current method of sensing and monitoring chemical and environmental toxins and biohazardous materials is accomplished using mass spectrometers. This method of detecting substances typically uses relatively large monitored equipment that is not typically amenable to situations where portable monitoring devices are needed. For instance, mass spectrometers are commonly used in an airport setting where items passing through security may be swabbed and the presence of controlled or banned substances is sensed. The mass spectrometer used is typically a permanent, or semi-permanent, sensing unit that is monitored by security personnel.

Of growing interest is the use of optical sensing devices to sense and monitor substances of interest. In many instances, these devices include a waveguide in which a beam of light is propagated. The optical characteristics of the device are influenced by variations at the surface of the waveguide, such as a change in the total reflection. Other types of optical sensors are based on the use of a sensing optical fiber in which the fiber serves as an optical transmission line that, in conjunction with a sensor device, detects the presence of various substances based on light transmission loss. These optical fibers provide for sensing along the length of the fiber.

In existing concepts, an optical sensor operates by transmitting light of a wavelength spectrum from a light source via a fiber to a sensing section, a sensor or sensor array. The light is then directed from the sensing section or sensor(s) to a tunable filter driven by a waveform generator which is scanned to detect the intensity of light within each wavelength band of the of the source light wavelength spectrum. A portion of the light, in the spectrum corresponding to a subset of wavelengths within the spectrum, i.e. a channel, is affected by the sensed condition or sensed substance in the sensor or sensing section. The peak of intensity of the light coming from the sensing section, or sensor(s) for each channel is detected and a digital pulse representative of the peak of the detected light in each channel is generated. The digital pulses are converted to a value which is proportional to the intensity of light in a channel centered at a particular wavelength. Using a model of the sensor's relationship of intensity versus wavelength for measurement of a particular parameter, a measurement value based on this parameter can be made. For example, a fiber optical sensing section may be used, with a fiber having an increased loss of a particular wavelength band in the presence of a hazardous gas. In this case, there will be less light in that particular wavelength band in the presence of the gas, and a dip in intensity will be observed at the detector at this wavelength, but not across the whole source spectrum. In this way, a measurement of the gas concentration can be made.

All-purpose, multi-gas optical sensor systems have been found to be very expensive, primarily because of the cost associated with the various light sources needed to illuminate a sensor or sensor array with light of the appropriate spectral bandwidth; that is, containing the large range of wavelengths needed to stimulate transitions in all the substances of interest. In addition, conventional optical fibers cannot be used for the sensing section without major modification, in that the light's electric field does not extend out into the environment, meaning that does it not interact significantly with the environment in which the sensor resides. Because of the light source power and spectral requirements, and because of the filter requirements, the cost, weight and volume are significant in prior art systems, which can limit the use of these systems in portable sensor applications or other environments in which a light weight or compact monitoring system is needed or desired, but a highly accurate sensor is required.

Accordingly, there exists a need for an improved optical fiber sensor system which avoids these prior art deficiencies and would be useful in a user friendly system such as a system which monitors chemical and environmental toxins and biohazardous materials. This invention relates to an optical sensor and method of using the sensor for the sensing and monitoring of chemical and environmental toxins and biohazardous materials in an atmosphere. In addition, there is a need for an improved optical fiber sensor system that could be used in the area of homeland security and battlefield security. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An apparatus is provided for an optical sensor positioned in an environment in which a contaminant particle is to be sensed, the optical sensor comprising a light source, at least one optical waveguide arranged in a resonant structure, a detector, and a substrate of choice. The substrate is preferably, but not limited to, silicon and at least some of the optical components are formed on, or attached to the silicon substrate. The light source is operable to emit light. The at least one optical waveguide includes a receiving end positioned to receive the light emitted from the light source and configured to allow the light to propagate there through. The detector is positioned and configured to detect absorption of the light propagating through the optical waveguide. The optical waveguide is of a diameter that an evanescent tail of the lightwave propagating there through extends into the environment and is reactive to the at least one contaminant particle in the environment.

In addition, an apparatus is provided for an optical resonant sensor for sensing one or more contaminant particles in an environment, the optical sensor comprising a light source operable to emit light, a first optical waveguide on a substrate, a second optical waveguide on a substrate, and an optical waveguide ring on a substrate, and a detector. All waveguides are configured to allow the light to propagate there through. The first optical waveguide has a receiving end positioned to receive the light emitted from the light source, a portion of the waveguide in the optical waveguide ring is positioned to receive light that is coupled from the first optical waveguide, and a portion of the second optical waveguide is positioned to receive light that is coupled from the waveguide in the optical waveguide ring. The first optical waveguide, the second optical waveguide and the optical waveguide ring form an optical resonator such that the evanescent tail of a lightwave propagating there through the optical resonator extends into the environment in which the optical resonant sensor is positioned and is sensitive to a contaminant particle in the environment. The detector is configured to detect the absorption of the light propagating through the optical resonator In another exemplary embodiment, an apparatus is provided for an optical resonant sensor for sensing one or more contaminant particles in an environment, the optical sensor comprising a light source operable to emit light of tunable frequency, a mirror mounted on a substrate, an optical fiber coil, and a detector. The optical fiber coil has a first end and a second end; each positioned adjacently to the mirror and fastened to the substrate, such as by fastening in v-grooves. The mirror and the optical fiber coil form an optical resonator, i.e. the mirror directs light into the first end of the fiber, the light propagates through the fiber coil exiting through the second end of the fiber. The mirror directs a large fraction of the light emerging from the second end into the first end. The optical fiber is designed such that a portion of its evanescent field extends into, and interacts with, the environment. The mirror is preferably slightly transmissive such that light is coupled from the light source into the resonator with high efficiency when the light source frequency is tuned to the resonance frequency of the resonator, formed by the mirror and the optical fiber coil. The detector is positioned such that it detects the fraction of light energy not dissipated in the optical resonator.

In addition, a method is provided for sensing one or more contaminant particles in an environment with an optical sensor. The method includes the steps of providing a light source, a first optical waveguide, a second optical waveguide, an optical waveguide ring disposed between the first optical waveguide and the second optical waveguide, and a detector. The first optical waveguide, the second optical waveguide and the optical waveguide ring form an optical resonator. The optical resonator, the light source, and the detector are provided to form an optical resonant sensor. The method further including the steps of positioning the optical resonant sensor in an environment for sensing one or more contaminant particles in the environment and transmitting a light in waveguides within the optical resonant sensor such that the evanescent tail of the of the light-wave propagating along the waveguide extends into the environment in which the optical sensor is positioned and is sensitive to a contaminant particle present in the surrounding environment.

BRIEF DESCRIPTION OF THE DRAWINGS

The present invention will hereinafter be described in conjunction with the following drawing figures, wherein like numerals denote like elements.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
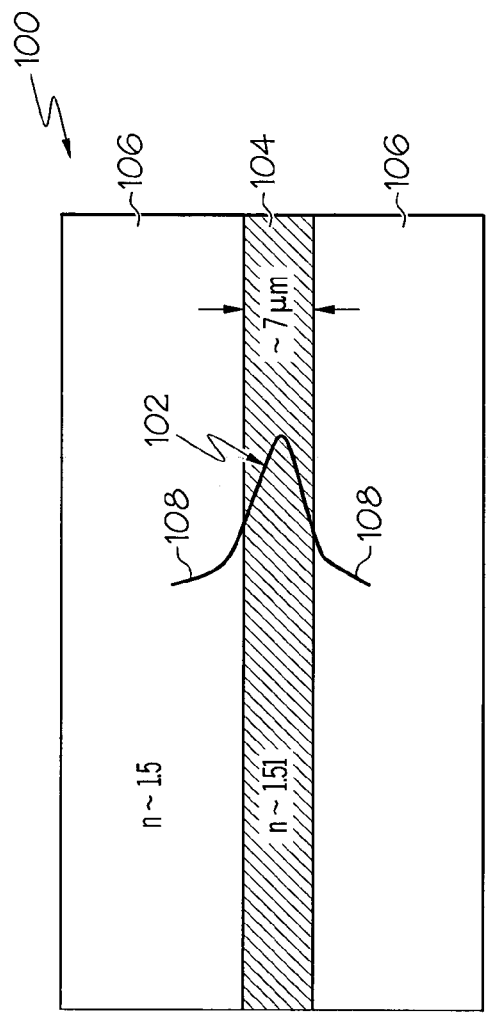
FIG. 1 is a schematic diagram illustrating a cross section of a conventional optical fiber for the transmission of light.

Referring to the drawings, illustrated in FIG. 1 is a conventional optical fiber 100 having a lightwave 102 depicted as traveling there through. In conventional fibers, signal-to-noise limitations have presented a problem in that a lightwave 102 traveling within fiber 100 does not interact strongly with the environment in which optical fiber 100 resides. Conventional optical fiber 100 is comprised of a glass material and includes at a central portion thereof, a core region 104. Core region 104 is generally formed of a doped glass material having an index of refraction that is higher than an index of refraction of a glass material 106 surrounding core region 104. The index difference is typically very small, on the order of 1%. Thus, in the depicted embodiment, glass material 106 has an index of refraction of n~1.5 and the glass material that comprises core region 104 is doped to have an index of refraction of n~1.51. Lightwave 102 travels more readily through the glass material having the higher index of refraction and thus travels through core region 104. The higher the index of refraction, the slower the movement of the light traveling there through. Core region 104 in essence serves as a "light pipe" in that the lightwave 102 traveling through core region 104 is buried deep inside the fiber 100 and is confined within that center region. Core region 104 is typically 5-10 microns in diameter and typically the mode field diameter of the intensity of the lightwave 102 is confined to a size comparable to the core dimension Conventional optical fiber 100 has an overall diameter of approximately 80 to 125 microns.

Figure 2:
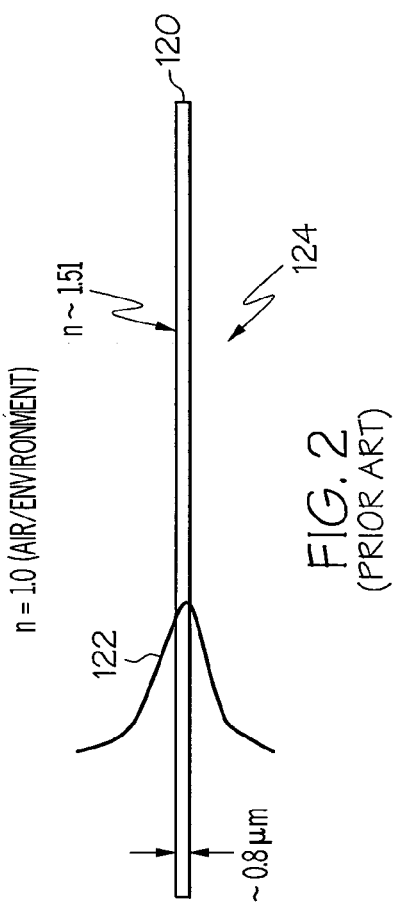
FIG. 2 is a schematic diagram illustrating a conventional nanofiber for the transmission of light.

As illustrated in FIG. 1, the presence of evanescent tails 108 of lightwave 102 can be seen extending outside of core region 104. In conventional optical fiber 100, a relatively large amount of glass material 106 separates the lightwave 102 from the environment. This results in the light wave 102 having little interaction or ability to experience the environment in which the optical fiber 100 resides. The burying of the lightwave 102 deep within the fiber 100 is design-specific in that typical applications of optical fibers do not want the lightwave 102 to appreciably interact with the environment. In the event lightwave 102 were to spread out to the surrounding environment and hence, interact with environment when optical fiber 100 is utilized as an optical sensor to sense the presence of a specific type of contaminant particle, the strength of interaction of the light with the contaminant particle being sensed will be dependent of the wavelength of the light. That is, some wavelengths of light would not be affected by the presence of the particle, whereas some wavelengths of light may be highly affected, being either strongly absorbed, or scattered by the particle. As previously stated, the problem that exists with conventional optical fiber sensors is that the light wave is too tightly confined within the glass to interact with the environment. It should be appreciated that the term "contaminant particle" will be used throughout this disclosure to encompass both harmful and non-harmful chemical and/or biological molecules that exist in an environment being sensed Referring now to FIG. 2, illustrated is a nanowire fiber 120 which is in itself known, but serves as a component of the present invention that operates as a sensor. During fabrication, an optical fiber is heated up and drawn down to a structure having a diameter on the order of the wavelength of light. In this particular embodiment, nanowire fiber 120 has a diameter of approximately 0.8 microns. The reduction in diameter of the optical fiber means that a lightwave 122 propagating through the nanowire fiber 120 cannot actually remain within nanowire fiber 120. It should be appreciated that nanowire fiber 120 doe not have a separate core region as previously described with the conventional optical fiber 100 of FIG. 1. Nanowire fiber 120 is formed of a glass material similar to a conventional optical fiber, except that in this particular embodiment there does not exist a center core region formed by doping. A single region of glass having a single index of refraction forms nanowire fiber 120. The surrounding environment, generally referenced 124, in which nanowire fiber 120 resides, now serves as the region having a lower index of refraction, thus forming a waveguide. As illustrated, the mode field of light 122 propagating through nanowire fiber 120 extends substantially out into the environment, or surrounding air, 124, so that it interacts with the environment 124 to a greater degree than the conventional optical fiber 100 of FIG. 1.

Nanowire fiber 120 is of a size that results in the electric field of the propagating lightwave 122 to extend outside the nanowire fiber 120. Thus, a lightwave 122 propagating through nanowire fiber 120 is very sensitive to the environment in which nanowire fiber 120 resides. This extension of the lightwave 122 into the environment makes nanowire fiber 120 amenable to sensing one or more contaminant particles present in the environment.

As previously stated, different types of particles or molecules that comprise a chemical, environmental or biohazard substances are responsive to specific wavelengths of light. Hence, one wavelength of light may not interact with molecules of a certain species, whereas light at another wavelength may strongly interact with it.

Figure 3:
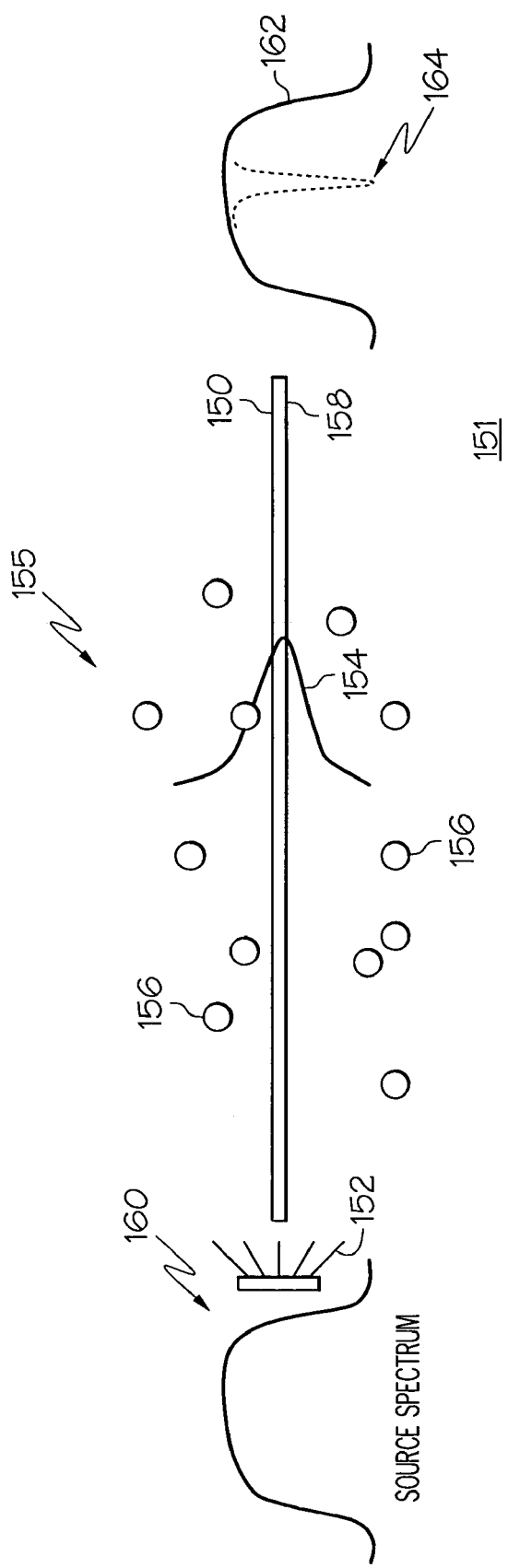
FIG. 3 is a schematic diagram illustrating an exemplary embodiment of a nanofiber optical sensor and the effected light transmission through the nanofiber according to the present invention.

Referring now to FIG. 3, illustrated is schematic representation of a nanowire fiber sensor 151. Nanowire fiber sensor 151 includes a nanowire fiber 150, which operates as a waveguide, and a broad-band light source 152. The spectrum of broad-band light source 152 is indicated by diagram 160. This type of light source supplies light over a broad range of frequencies or wavelengths. During the sensor operation, a broadband lightwave 154 supplied from light source 152 propagates through nanowire fiber 150. A plurality of contaminant particles 156 are illustrated as being present in an environment 155 in which nanowire fiber sensor 151 resides.

As the broadband light 154 propagates through nanowire fiber 150, one wavelength might interfere with a contaminant particle in terms of the particles 156 absorbing the wavelength, resulting in a drop out or loss of light of that particular wavelength at a terminal end 158 of nanowire fiber 150. In determining the presence of a specific type of contaminant particle 156, one would observe the spectrum of light at the output, noting that some portion of the spectrum is no longer present, or attenuated, at terminal end 158 as illustrated in diagram 162. Diagram 162 illustrates the absorption band at the terminal end 158 of the nanowire fiber 150 and indicates a drop off 164 for light at a specific wavelength of the source spectrum 154. A determination of the particular contaminant present can be made as a result of this attenuation at a specific wavelength, knowing that different species produce attenuation at different wavelengths. The nanowire fiber 150 in effect becomes a notch filter. The depth of the notch in the spectrum as illustrated by diagram 162, and the center frequency of the notch are indicative of the concentration of a specific contaminant and the type, respectively.

Figure 4:
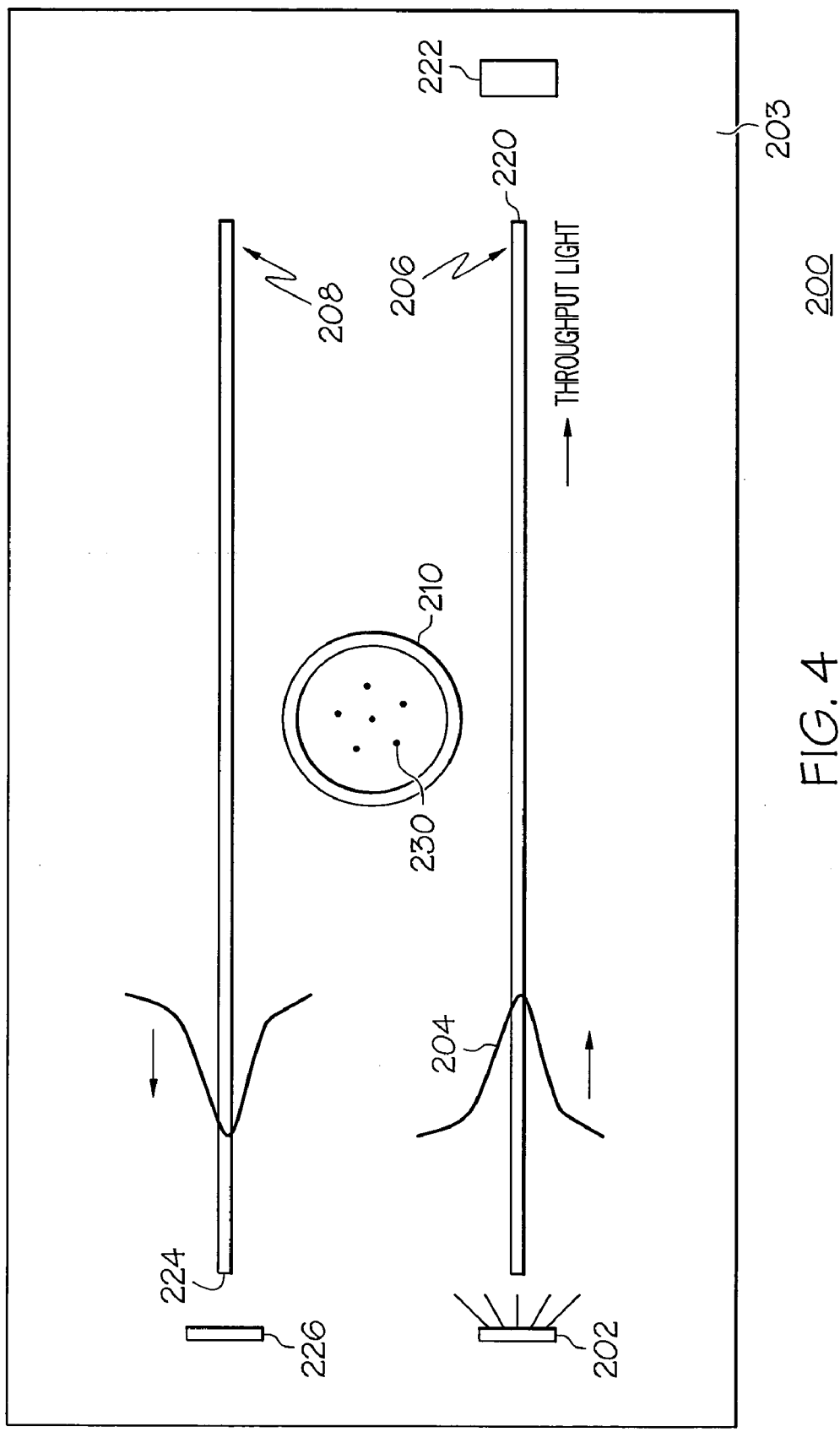
FIG. 4 is a schematic diagram illustrating an exemplary embodiment of an optical resonant sensor according to the present invention.

FIG. 4 illustrates an embodiment of an optical resonant sensor according to the present invention. To intensify the above effects and boost the sensing sensitivity, a ring resonator may be constructed for use with the optical nano-wire waveguide or nano-fiber of FIGS. 2 and 3. The resonant sensor includes a ring resonator that requires a narrow band light source, in which the center frequency of the light source is swept across a resonance of the resonator. The ring resonator is fabricated to resonate in a particular frequency range that will be absorbed by a sensed molecular contaminant particle. In the absence of the contaminant, the ring will have a sharp resonance, indicative of low loss inside the resonator. In the presence of the contaminant, the ring's ability to resonate is highly degraded by absorption losses, the light's electric field build-up inside the resonator greatly diminishes, and the resonance line shape broadens as will be shown.

Referring more specifically to FIG. 4, illustrated is an optical resonant sensor 200 that is formed as a resonator device. In this particular embodiment, optical resonant sensor 200 uses a monochromatic light source 202, also referred to as a single frequency light source. It should be understood that while light source 202 supplies single frequency lightwaves, it may be static in time so as to be a fixed frequency light source, or it may scan frequencies over a period of time. More specifically, the frequency of a resulting lightwave 204 may be a single value at any single point in time, but can be ramped up or down according to the frequency desired for sensing.

Optical resonant sensor 200 is formed as a ring resonator sensor, and includes a first waveguide 206 and a second waveguide 208 through which lightwave 204 travels. More particularly, optical resonant sensor 200 includes an input waveguide 206 and an output waveguide 208. Waveguides 206 and 208 can be formed as three-dimensional glass tubes, such as optical nanowire fibers as previously detailed with regard to FIGS. 2 and 3, or they could be formed as a waveguide deposited on a substrate, such as a chip, and formed of a polymer based material using standard lithography techniques, formed using waveguides in silicon, or formed on a chip using silicon waveguides with silicon dioxide thin films. In the embodiment shown in FIG. 4, optical resonator 200 is formed on a substrate 203. Substrate 203 is preferably a silicon substrate or silicon-on-insulator substrate.

Optical resonant sensor 200 additionally includes an optical waveguide ring 210, which is a waveguide arranged in a closed path loop. Optical waveguide ring 210 and portions of waveguides 206 and 208 that are in close proximity to optical waveguide ring 210 form an optical resonator will resonate when lightwave 204 traveling through input waveguide 206 is of a wavelength such that an integer number of wavelengths will fit inside the ring 210. This is the constructive interference condition necessary for resonance. When lightwave 204 resonates, it enters the optical ring 210 and constructively interferes, causing the light energy to be strongly increased inside optical ring 210. This resonant condition only happens at discrete wavelengths; when an integer number of wavelengths fit inside optical waveguide ring 210. When the frequency of lightwave 204 is off-resonance, the lightwave will dissipate inside the optical waveguide ring 210, essentially passing straight through waveguide 206 through a transmission port 220.

Figure 5:
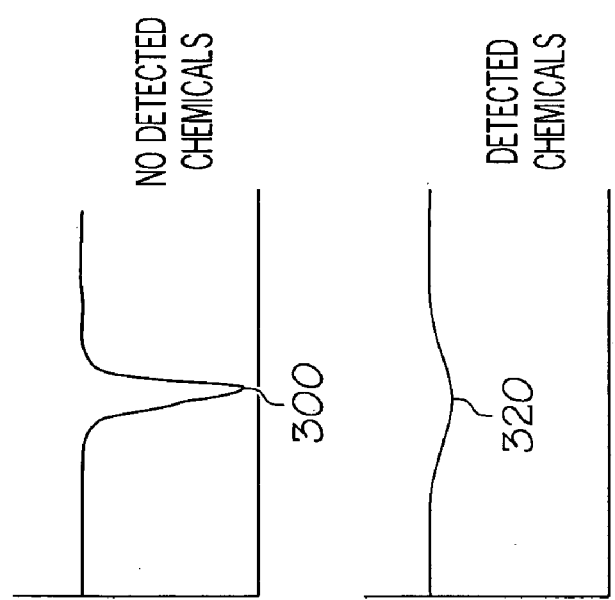

Referring again to FIG. 4, during operation and the resonance condition, lightwave 204 enters the optical ring 210 and ultimately travels back along waveguide 208. During this resonant condition, a high electrical field is built up inside the ring 210. With the right frequency of light from light source 202, a majority of the light will enter optical ring 210 and start circulating. The electric field inside the ring will dramatically increase. There are dissipative losses inside the ring, such as losses due to scattering. Since light enters the optical waveguide ring, less light is transmitted to the output port 220 of waveguide 206. A resonance dip will be detected at a transmission port 220 of waveguide 206. In that light is now circulating in the ring, it is available for coupling to waveguide 208, and as the light source frequency is scanned across the resonance frequency of the optical resonator a resonance peak appears at port 224 of waveguide 208. A detector 222 will detect a drop in the detected light signal near resonance as illustrated in FIG. 5 by a resonance dip 300 at output port 220, or illustrated in FIG. 6 by a peak 400 in the output at port 224. The sharpness of the resonance dip and resonance peak depends on the losses inside the ring 210 (FIG. 4). When light is not constructively interfering inside the resonator loop, the detector 222 will see virtually all the light, assuming the waveguide 206 has negligible loss, because it is off-resonance.

The light buildup inside optical waveguide ring 210 will ultimately either dissipate through scattering or exit sensor 200 through port 224 of waveguide 208. Away from resonance center, virtually all of the lightwave 204 travels through waveguide 206 and exits at port 220, assuming losses in waveguide 206 are negligible. Thus there is virtually no light output from port 224. At resonance, there is light energy inside ring 210, so there is an abundance of light energy available for coupling to waveguide 208, and light coupled from ring 210 into waveguide 208 exits through the port 224 of waveguide 208.

During operation of optical fiber sensor 200, sensor 200 is exposed to an air-borne substance that may or may not contain a contaminant particle or molecular particle. A light source of a wavelength that will interact with the particle being sensed is used for light source 202. For example, if a specific type of molecular contaminant has a response to light at 1.5 microns, a 1.5 micron light source is used for light source 202. When the molecular particles see that specific wavelength, they will scatter it, or absorb it, thus extracting energy out of the optical sensor 200. This will in turn change the resonance line shapes observed at output port 224 and 220 respectively. In each case, in the presence of the contaminant substance, the resonance will broaden, and its quality factor (Q) and its finesse will degrade with induced losses in ring 210.

Figure 6:
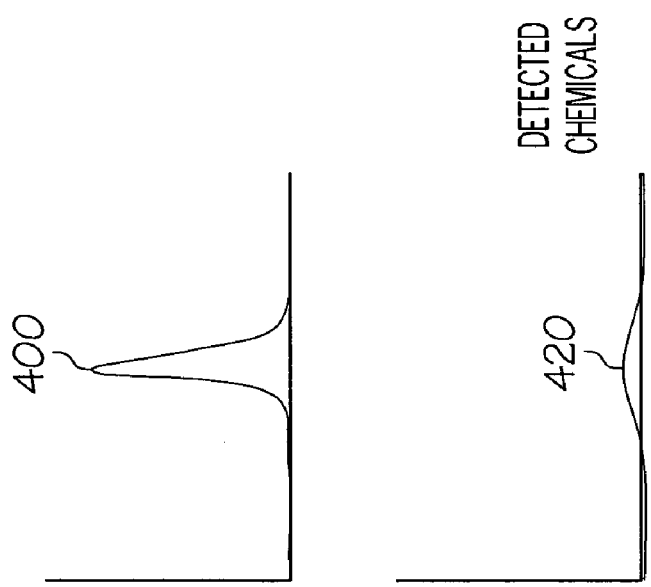
FIGS. 5 and 6 are diagrams illustrating effected light transmission through the optical sensor of FIG. 4 in accordance with embodiments of the present invention.

As previously stated, the sharpness of the resonance dip 300 (FIG. 5) and resonance peak 400 (FIG. 6) depends on the losses inside the ring 210. If there is very little optical loss inside the ring, then the dip 300 is sharp as seen at port 220 and the peak 400 is sharp as seen at port 224. When some contaminant particles 230 are present so that the lightwave 204 interacts with these particles when traveling within optical ring 210, the light will be scattered and the sharpness of the resonance dip will degrade or the resonance line shapes will disappear altogether. In the former case, a more shallow and wide dip, as seen by dip 320 of FIG. 5 is observed at port 220 and a shallow and wide peak 420 of FIG. 6 is observed at port 224. This condition is described as "loss" and is an indicator that a contaminant substance sought to be sensed is present. The optical resonator sensor 200 is a very sensitive measure of whether there is a specific type of contaminant particle(s) in the vicinity of the sensor. The type and concentration of the sensed contaminant particle can be determined by the wavelength of light for which the resonator finesse degraded, and the diminished light circulating in the ring, or the resonance lineshape sharpness.

Figure 7:
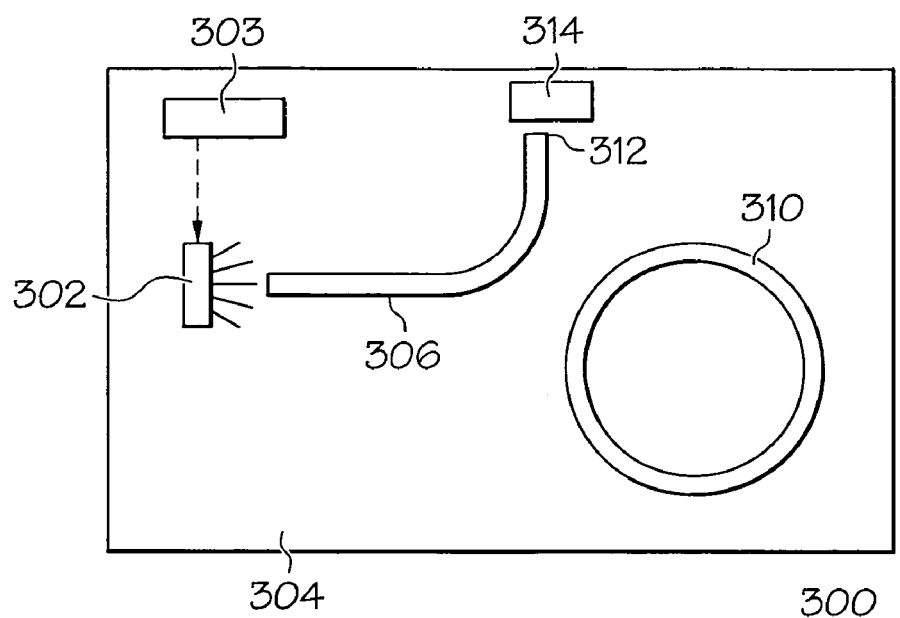
FIG. 7 is a schematic diagram illustrating an exemplary embodiment of an optical resonant sensor according to the present invention.

Referring now to FIG. 7, illustrated is an alternate embodiment of an optical resonant sensor 300 that is formed as a resonator device. In this particular embodiment, optical resonant sensor 300 uses a monochromatic light source 302, coupled to drive electronics 303. Light source 302 is also referred to as a single frequency light source. It should be understood that while light source 302 supplies single frequency lightwaves, it may be static in time so as to be a fixed frequency light source, or it may scan its frequency over a period of time Optical resonant sensor 300 is formed as a ring resonator sensor, and includes a single waveguide 306 through which a lightwave travels. Waveguide 306 can be formed as three-dimensional glass tubes, such as optical nanowire fibers as previously detailed with regard to FIGS. 2 and 3, or as a waveguide deposited on a substrate, such as a chip, as previously described with regard to FIG. 4. In the embodiment shown in FIG. 7, optical resonator 300 is formed on a substrate 304. Substrate 304 is preferably a silicon substrate or silicon-on-insulator substrate.

Optical resonant sensor 300 additionally includes an optical waveguide ring 310, which is a waveguide arranged in a closed path loop. Optical waveguide ring 310 and portions of waveguide 306 that are in close proximity to optical waveguide ring 310 form an optical resonator that will resonate when a lightwave traveling through input waveguide 306 is of a wavelength such that an integer number of wavelengths will fit inside the ring 310. When the lightwave resonates, it enters the optical ring 310 and constructively interferes, causing the light energy to be strongly increased inside optical ring 310. When the frequency of the lightwave is off-resonance, the lightwave will dissipate inside the optical waveguide ring 310, essentially passing straight through waveguide 306 through a transmission port 312.

During operation, a resonance dip will be detected at transmission port 312 of waveguide 306. A detector 314 will detect a drop in the detected light signal near resonance at output port 312 or by a peak in the output at port 312. The sharpness of the resonance dip and resonance peak depends on the losses inside the ring 310. When light is not constructively interfering inside the resonator ring 310, the detector 314 will see virtually all the light, assuming the waveguide 306 has negligible loss, because it is off-resonance.

Sensor 300 operates similar to sensor 200 of FIG. 4, in that during operation, sensor 300 is exposed to an air-borne substance that may or may not contain a contaminant particle or molecular particle. A light source of a wavelength that will interact with the particle being sensed is used for light source 302. When the molecular particles see that specific wavelength, they will scatter it, or absorb it, thus extracting energy out of the optical sensor 300. This will in turn change the resonance lineshapes observed at output port 312. In each case, in the presence of the contaminant substance, the resonance will broaden, and its quality factor (Q) and finesse will degrade with induced losses in ring 310.

Figure 8:
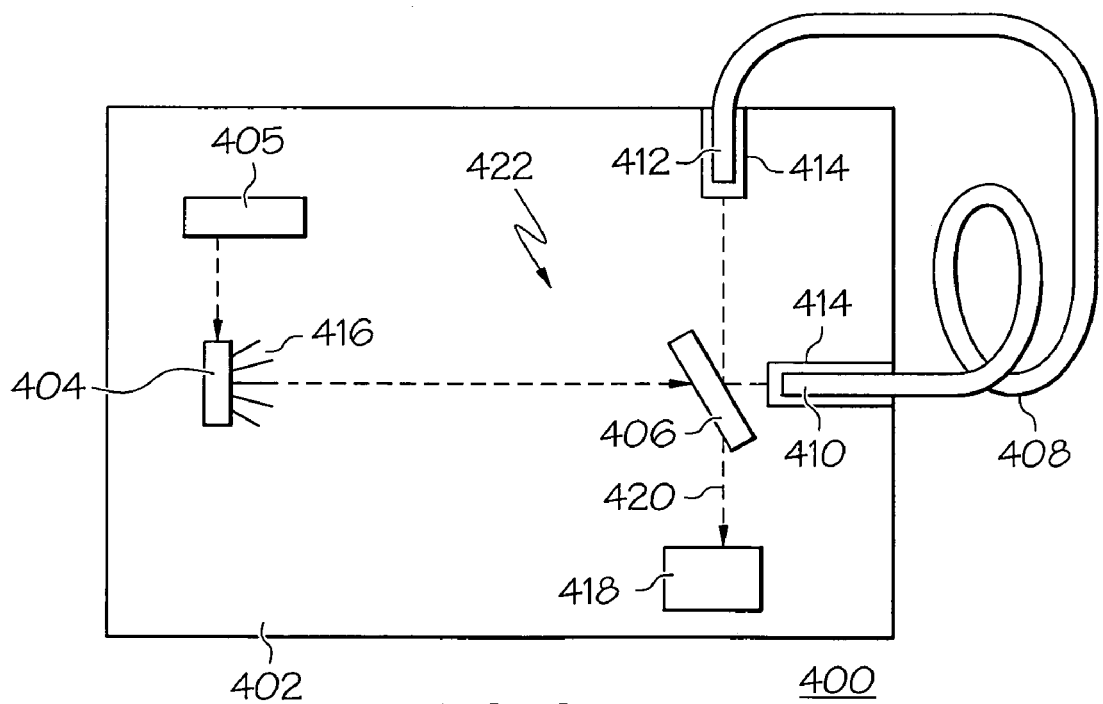
FIG. 8 is a schematic diagram illustrating an exemplary embodiment of an optical resonant sensor according to the present invention.

Referring now to FIG. 8, illustrated is yet another alternative embodiment of a resonant sensor according to the present invention. More specifically, illustrated is a resonant sensor 400. Resonant sensor 400 is formed on a substrate 402, similar to that previously described with the first and second embodiments. Substrate 402 in this particular embodiment is a silicon substrate, or a silicon-on-insulator substrate because of fabrication process efficiency and the ability to fabricate optics (so-called "silicon optical bench") and electronics on the same substrate. Although silicon is the substrate and material system of preference it is acknowledged that other materials having suitable properties beside silicon may be considered without loss of generality.

Sensor 400 includes a light source 404, including drive electronics 405. Light source 404 is operable to emit light of tunable frequency. A mirror 406 is mounted on the substrate 402. Mirror 402 is a high reflectivity mirror having a non-zero transmission coefficient. An optical fiber coil 408, having a first end 410 and a second end 412 positioned adjacently to the mirror 406 and fastened to the substrate 402. Optical fiber coil 408 operates in this embodiment as an optical waveguide for the transmission of light there through. The first end 410 and the second end 412 of fiber 408 may be very precisely and stably located, in for example, v-shaped grooves 414 etched into the surface of the substrate 402 relative to an input light beam 416 or the mirror 408. The mirror 406 and the optical fiber coil 408 form an optical resonator 422 that operates with the mirror 408 directing light 416 into the first end 410 of the fiber 408, the light 416 propagates through the fiber coil 408 exiting through the second end of the fiber. The mirror 406 is positioned to reflect a large fraction of the light emerging from the second end 412 and is reflected back into the first end 410. The optical fiber 408 is designed such that a portion of its evanescent field extends into, and interacts with, the environment. The mirror 406 is preferably transmissive such that light is coupled from the light source 404 into the resonator 422 with high efficiency when the light source 404 frequency is tuned to the resonance frequency of the resonator 422, formed by the mirror 406 and, the optical fiber coil 408.

A detector 418 is positioned such that it detects the fraction of light energy 420 not dissipated in the optical resonator 422. The detector 418 preferably includes of an optical photodetector and signal processing electronics for interpreting its output. The fraction of light not dissipated in optical resonator 422 is at a maximum when the light source 404 frequency is tuned away from the resonance frequency of the resonator 422, and a minimum when the light source 404 frequency is tuned to the resonance frequency of the resonator 422, thus a "resonance dip" line shape, as previously described, is observed at the detector 418. The sharpness of the resonance dip, namely its steepness with a variation in input light source frequency (for a given resonator length) is exemplified by its finesse. The finesse is higher for a steeper slope. The finesse of the resonator 422 is, in turn, indicative of the round trip losses for light 416 propagating in the resonator. Thus, while the light source frequency is scanned or tuned across the resonator resonance line shape, a measure of the finesse or line width is measured. With low loss in the optical fiber coil 408, the optical resonator has high finesse indicative of the absence of the monitored contaminant in the environment, and the width of the resonance line shape of the resonator is minimized. In the presence of contaminant particles in the environment, the resonance line shape broadens, i.e. the finesse is degraded. The degree of degradation of the finesse is a measure of the concentration of the contaminant near the optical fiber 408.

As discussed above, the preferred embodiments use silicon optical bench techniques, in which a variety of precision optical structures may be etched or formed on the surface of the substrate to be integrated with the substrate. Additionally, external optical components may be precisely mounted on the surface of the substrate or formed on the substrate or on additional material layers above a base layer of the substrate. Many of the components of the resonant optical may be integrated into or onto the substrate or formed onto or mounted onto the substrate. In this way, a compact, economical sensor may be realized.

It is noted that the light source in the present invention needs to be a narrow spectral line width source. One possibility for a compact, inexpensive source is a laser diode, mounted in an external cavity. Such an external cavity can be used to narrow the line width. External cavity lasers diodes are ideal for the silicon optical bench platform, in that the diode itself may be mounted on the surface of the substrate, the external reflectors can be formed or attached to the surface, and the laser light may be coupled into a waveguide to guide the light to the resonator. Alternatively, light from the laser diode may be directed in free space to the resonator, or to fiber via optics that are placed in the tiny optical bench. Also alternatively, the laser diode and one or more external elements may be mounted on an intermediate substrate which is then attached to the primary substrate.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. An optical resonant sensor for sensing one or more contaminant particles in an environment, the optical resonant sensor comprising:
   a substrate;
   a monochromatic light source operable to emit light on said substrate of a wavelength interactive with the one or more contaminant particles being sensed;
   an input optical waveguide on said substrate having a receiving end positioned to receive the light emitted from the monochromatic light source and configured to allow the light to propagate there through toward an output transmission port;
   an optical waveguide ring on said substrate and positioned to receive at least a portion of the light emitted from the monochromatic light source;
   an output optical waveguide on said substrate and positioned to receive light from the optical waveguide ring and configured to allow the light to propagate there through toward an output transmission port;
   a first detector configured to measure a resonance dip at the output transmission port of the input optical waveguide;
   a second detector configured to measure a resonance peak at the output transmission port of the output optical waveguide;
   wherein at least the input optical waveguide and the optical waveguide ring form an optical resonator in which that the evanescent tail of a lightwave propagating there through the optical waveguide ring extends into the environment in which the optical resonant sensor is positioned and is sensitive to a contaminant particle in the environment.

2. The optical resonant sensor of claim 1, wherein said substrate is one of a silicon substrate or a silicon-on-insulator substrate.

3. The optical resonant sensor of claim 1, wherein the environment in which a contaminant particle is to be sensed is air.

4. The optical resonant sensor of claim 3, wherein the contaminant particle is one of a chemical contaminant or a biological contaminant.

5. The optical resonant sensor of claim 1, wherein the optical sensor is a portable device.

6. The optical resonant sensor of claim 1, wherein at least one of the input optical waveguide and the output optical waveguide is formed as three-dimensional glass fiber.

7. The optical resonant sensor of claim 1, wherein the input-optical waveguide, the output optical waveguide, and the optical waveguide ring are photolithographically deposited polymer components formed on a semiconductor chip.

8. The optical resonant sensor of claim 1, wherein the input-optical waveguide, the output optical waveguide, and the optical waveguide ring are formed as silicon waveguides on a silicon substrate.

9. The optical resonant sensor of claim 1, wherein the light source is a single frequency laser.

* * * * *